United States Patent
Howbert et al.

(10) Patent No.: US 9,216,192 B2
(45) Date of Patent: Dec. 22, 2015

(54) TOLL-LIKE RECEPTOR AGONIST FORMULATIONS AND THEIR USE

(75) Inventors: J. Jeffry Howbert, Bellevue, WA (US); Muralikrishna Duvvuri, Durham, NC (US); Robert Hershberg, Seattle, WA (US); Gregory Dietsch, Snohomish, WA (US)

(73) Assignee: VentiRx Pharmaceuticals, Inc., Seattle, WA (US)

( * ) Notice: Subject to any disclaimer, the term of this patent is extended or adjusted under 35 U.S.C. 154(b) by 484 days.

(21) Appl. No.: 13/550,192

(22) Filed: Jul. 16, 2012

(65) Prior Publication Data

US 2013/0018042 A1 Jan. 17, 2013

Related U.S. Application Data

(63) Continuation of application No. 12/533,596, filed on Jul. 31, 2009, now Pat. No. 8,242,106.

(60) Provisional application No. 61/137,694, filed on Aug. 1, 2008.

(51) Int. Cl.

| | | |
|---|---|---|
| C07D 223/16 | (2006.01) |
| C07D 227/10 | (2006.01) |
| A61K 31/55 | (2006.01) |
| A61K 31/724 | (2006.01) |
| A61K 9/00 | (2006.01) |
| A61K 9/08 | (2006.01) |
| A61K 9/19 | (2006.01) |
| A61K 47/48 | (2006.01) |
| B82Y 5/00 | (2011.01) |
| C08B 37/16 | (2006.01) |

(52) U.S. Cl.
CPC .............. *A61K 31/724* (2013.01); *A61K 9/0019* (2013.01); *A61K 9/08* (2013.01); *A61K 9/19* (2013.01); *A61K 31/55* (2013.01); *A61K 47/48969* (2013.01); *B82Y 5/00* (2013.01); *C07D 223/16* (2013.01); *C08B 37/0012* (2013.01)

(58) Field of Classification Search
CPC .............................. A61K 31/55; C07D 223/16
See application file for complete search history.

(56) References Cited

U.S. PATENT DOCUMENTS

| | | | |
|---|---|---|---|
| 6,043,238 A | 3/2000 | Cooper et al. |
| 7,691,877 B2 * | 4/2010 | Jones et al. | .................. 514/303 |
| 7,718,695 B2 * | 5/2010 | Kim et al. | ..................... 514/475 |
| 8,242,106 B2 * | 8/2012 | Howbert et al. | ......... 514/213.01 |
| 2007/0197478 A1 | 8/2007 | Jones et al. |
| 2008/0008682 A1 | 1/2008 | Chong et al. |
| 2008/0057074 A1 | 3/2008 | Takaoka et al. |
| 2008/0234251 A1 * | 9/2008 | Doherty et al. | .......... 514/213.01 |

FOREIGN PATENT DOCUMENTS

| | | |
|---|---|---|
| EP | 0825186 B1 | 2/1998 |
| EP | 1790637 A1 | 5/2007 |
| EP | 1849781 A1 | 10/2007 |
| WO | WO-9612493 A1 | 5/1996 |
| WO | WO-9855148 A1 | 12/1998 |
| WO | WO-03007955 A2 | 1/2003 |
| WO | WO-2005009973 A1 | 2/2005 |
| WO | WO-2005035534 A1 | 4/2005 |
| WO | WO-2007024612 A2 | 3/2007 |
| WO | WO-2007040840 A2 | 4/2007 |
| WO | WO-2007096151 A2 | 8/2007 |
| WO | WO-2007128460 A1 | 11/2007 |
| WO | WO-2008024892 A2 | 2/2008 |
| WO | WO-2008109177 A2 | 9/2008 |
| WO | WO-2008109180 A2 | 9/2008 |
| WO | WO-2008109181 A2 | 9/2008 |

OTHER PUBLICATIONS

Challa, R. et al., "Cyclodextrins in Drug Delivery: An Updated Review," *AAPS PharmaSciTech*, vol. 6, No. 2, Oct. 14, 2005, pp. E329-E357.
Czarniecki, M. "Small Molecule Modulators of Toll-like Receptors". *J. Med. Chem.*, vol. 51:6621-6626 (2008).
Rajewski, R. et al., "Pharmaceutical Applications of Cyclodextrins. 2. In Vivo Drug Delivery," *Journal of Pharmaceutical Sciences*, vol. 85, No. 11, Nov. 1, 1996, pp. 1142-1169.

* cited by examiner

*Primary Examiner* — Eric Olson
(74) *Attorney, Agent, or Firm* — Cooley LLP; Heidi A. Erlacher; Lian Ouyang

(57) ABSTRACT

The present invention is directed generally to stable formulations of a TLR agonist preferably a TLR7 or a TLR8 agonist, for use in the treatment of cancer, preferably solid tumors and lymphomas. Specifically, the present invention is directed to stable formulations of up to 50 mg/ml of a TLR agonist which comprise a cyclodextrin.

15 Claims, No Drawings

TOLL-LIKE RECEPTOR AGONIST FORMULATIONS AND THEIR USE

1. RELATED APPLICATIONS

This application is a continuation application of U.S. application Ser. No. 12/533,596 (allowed), filed Jul. 31, 2009, which claims priority under 35 U.S.C. 119(e) to U.S. Application No. 61/137,694, filed Aug. 1, 2008. The entire contents of the above-identified applications are hereby incorporated by reference.

2. FIELD OF THE INVENTION

The present invention is directed to pharmaceutical formulations of toll-like receptor (TLR) agonists and their use.

3. BACKGROUND OF THE INVENTION

Toll-like receptors (TLRs) are a family of type I transmembrane proteins whose in vivo activation initiates an innate immune response involving specific cytokines, chemokines and growth factors. While all TLRs can activate certain intracellular signaling molecules such as nuclear factor kappa beta (NF-kB) and mitogen activated protein kinases (MAP kinases), the specific set of cytokines and chemokines released appears to be unique for each TLR. TLR7, 8, and 9 comprise a subfamily of TLRs which are located in endosomal or lysosomal compartments of immune cells such as dendritic cells and monocytes. Specifically, TLR7 is expressed by plasmacytoid dendritic cells and to a lesser extent by monocytes, and TLR8 is expressed by monocytes as well as by monocyte-derived dendritic cells and myeloid dendritic cells. This subfamily mediates recognition of microbial nucleic acids, such as single stranded RNA. Agonists of TLR7 and/or TLR8 stimulate the production of various inflammatory cytokines including interleukin-6, interleukin-12, tumor necrosis factor-alpha, and interferon-gamma. Such agonists also promote the increased expression of co-stimulatory molecules such as CD40, CD80, and CD86, major histocompatibility complex molecules, and chemokine receptors. The type I interferons, IFNα and IFNβ, are also produced by cells upon activation with TLR7/8 agonists.

Small, low-molecular weight (less than 400 Daltons) synthetic imidazoquinoline compounds which resemble the purine nucleotides adenosine and guanosine were the first TLR7 and TLR8 agonists to be identified. A number of these compounds have demonstrated anti-viral and anti-cancer properties. For example, the TLR7 agonist imiquimod (ALDARA™) was approved by the U.S. Food and Drug Administration as a topical agent for the treatment of skin lesions caused by certain strains of the human papillomavirus. Imiquimod may also be useful for the treatment of primary skin cancers and cutaneous tumors such as basal cell carcinomas, keratoacanthomas, actinic keratoses, and Bowen's disease. The TLR7/8 agonist resiquimod (R-848) is being evaluated as a topical agent for the treatment of human genital herpes.

4. SUMMARY OF THE INVENTION

The present invention is directed generally to formulations of pharmaceutical compositions containing a benzo[b]azepine TLR agonist for use in the treatment of cancer, preferably solid tumors and lymphomas, and for other uses including the treatment of certain skin conditions or diseases, such as atopic dermatitis, the treatment of infectious diseases, preferably viral diseases, and for use as adjuvants in vaccines formulated for use in cancer therapy and in the treatment of infectious diseases. Specifically, the present invention is directed to stable formulations of a benzo[b]azepine TLR agonist, preferably a TLR7 or a TLR8 agonist. In preferred embodiments, the benzo[b]azepine TLR7 or TLR8 agonist is used for the treatment of cancer and the cancer is selected from the group consisting of ovarian cancer, breast cancer, head and neck cancer, renal cancer, bladder cancer, hepatocellular cancer, and lymphoma.

Preferably, the benzo[b]azepine TLR agonist is formulated at a concentration of from about 0.5 mg/ml to about 50 mg/ml, from about 1 mg/ml to about 40 mg/ml, or from about 2 mg/ml to about 15 mg/ml. In certain embodiments, the benzo[b]azepine TLR agonist is formulated at a concentration of from about 0.5 mg/ml to about 10 mg/ml, from about 0.5 mg/ml to about 8 mg/ml, from about 0.5 mg/ml to about 6 mg/ml, from about 0.5 mg/ml to about 4 mg/ml, or from about 0.5 mg/ml to about 2 mg/ml. In certain embodiments, the benzo[b]azepine TLR agonist is formulated at a concentration of about 0.5 mg/ml, about 1 mg/ml, about 2 mg/ml, about 4 mg/ml, about 6 mg/ml, about 8 mg/ml, about 10 mg/ml, about 15 mg/ml, about 20 mg/ml, about 25 mg/ml, about 30 mg/ml, about 40 mg/ml, or about 50 mg/ml. Preferably, the formulation comprises about 1-30%, 5-15%, or 5-10% weight/volume (w/v) of a cyclodextrin, preferably a β-cyclodextrin, and most preferably sulfobutylether β-cyclodextrin. In certain embodiments, the formulation comprises 1%, 5%, 10%, 15%, 20%, 25%, or 30% w/v of a cyclodextrin, preferably a β-cyclodextrin, and most preferably sulfobutylether β-cyclodextrin. In a particular embodiment, the formulation is an aqueous solution comprising the benzo[b]azepine TLR agonist at a concentration of at least 2 mg/ml. In a further embodiment, the formulation comprises 15% w/v of a cyclodextrin, preferably a β-cyclodextrin, and most preferably sulfobutyl ether β-cyclodextrin. In preferred embodiments, the formulation is suitable for injection in a mammal, preferably a human. In particular embodiments, injection is by a subcutaneous route, an intramuscular route, or transdermal route. In certain embodiments, the formulation is suitable for intravenous administration.

In certain embodiments, the pH of the benzo[b]azepine TLR agonist formulation is acidic (meaning less than 7). Preferably, the pH of the benzo[b]azepine TLR agonist formulation is from about 5.0 to about 7, preferably from about 5.5 to about 6.5. In a particular preferred embodiment, the pH is 6.5. In one embodiment, the benzo[b]azepine TLR agonist formulation is a solid, a liquid or lyophilized formulation suitable for injection in a mammal, preferably a human. In one embodiment, the formulation is sterile. In certain embodiments, the present formulations are stable at temperatures ranging from about 20 to 25° C. for at least 1 week and the formulation is stable for at least 2 weeks at about 2 to 8° C.

The present invention also provides lyophilized formulations of a benzo[b]azepine TLR agonist which when reconstituted in aqueous solution are substantially soluble. Preferably, the reconstituted formulation is suitable for injection in a mammal, preferably a human. In particular embodiments, injection is by a subcutaneous route, an intramuscular route, or transdermal route. In certain embodiments, the formulation is suitable for intravenous administration.

In certain preferred embodiments, the benzo[b]azepine TLR agonist formulation comprises one or more of the following benzo[b]azepine TLR agonists: (1E, 4E)-ethyl 2-amino-8-(perfluoroethyl)-3H-benzo[b]azepine-4-carboxylate; (1E, 4E)-2-amino-N,N-bis(2-methoxyethyl)-8-(perfluoroethyl)-3H-benzo[b]azepine-4-carboxamide; (1E, 4E)-2-amino-N,N-diethyl-8-(perfluoroethyl)-3H-benzo[b]
azepine-4-carboxamide; (1E, 4E)-2-amino-8-(perfluoroethyl)-N,N-dipropyl-3H-benzo[b]azepine-4-carboxamide;
(1E, 4E)-2-amino-N-ethyl-8-(perfluoroethyl)-3H-benzo[b]
azepine-4-carboxamide; (1E, 4E)-2-amino-8-(perfluoroethyl)-N-propyl-3H-benzo[b]azepine-4-carboxamide; (1E,
4E)-ethyl 2-amino-8-(pyrrolidine-1-carbonyl)-3H-benzo[b]
azepine-4-carboxylate; (1E, 4E)-ethyl 2-amino-8-(4-(methoxycarbonyl)phenyl)-3H-benzo[b]azepine-4-carboxylate;
(1E, 4E)-ethyl 2-amino-8-(4-(methylcarbamoyl)phenyl)-3H-benzo[b]azepine-4-carboxylate; (1E, 4E)-2-amino-N,N-dipropyl-8-(4-(pyrrolidine-1-carbonyl)phenyl)-3H-benzo[b]
azepine-4-carboxamide; and pharmaceutically acceptable
salts thereof. In a particular embodiment, the benzo[b]
azepine TLR agonist is (1E, 4E)-2-amino-N,N-dipropyl-8-(4-(pyrrolidine-1-carbonyl)phenyl)-3H-benzo[b]azepine-4-carboxamide and pharmaceutically acceptable salts thereof.

The present invention further provides methods for the treatment of cancer by administering to a subject, preferably a human subject, a benzo[b]azepine TLR agonist formulation of the present invention, which contains a cyclodextrin. In a preferred embodiment, the benzo[b]azepine TLR agonist formulation is administered in combination with one or more additional treatment modalities, where the modalities are selected from a chemotherapeutic agent, a cytokine, an antibody, hormonal therapy, or radiation therapy. In one embodiment, the benzo[b]azepine TLR agonist formulation is administered as part of a regimen for the treatment of a solid tumor. In a further embodiment, the solid tumor is a form of cancer selected from among ovarian cancer, breast cancer, head and neck cancer, renal cancer, bladder cancer, hepatocellular cancer, or lymphoma. In one embodiment, the benzo[b]azepine TLR agonist formulation is administered as part of a regimen for the treatment of a lymphoma. In one embodiment, the lymphoma is Hodgkin's lymphoma. In another embodiment, the lymphoma is non-Hodgkin's lymphoma. In another embodiment, the benzo[b]azepine TLR agonist formulation is used as a vaccine adjuvant for the treatment of cancer. In certain embodiments of the methods for the treatment of cancer, the benzo[b]azepine TLR agonist formulation is administered by injection or intravenously. In particular embodiments, injection is by a subcutaneous route, an intramuscular route, or a transdermal route. In a particular embodiment, the formulation is administered by subcutaneous injection.

The present invention also provides methods for the treatment of atopic dermatitis by administering to a subject, preferably a human subject, a benzo[b]azepine TLR agonist formulation of the present invention, which contains a cyclodextrin. According to this embodiment, the route of administration is preferably subcutaneous or topical.

The present invention also provides methods for the treatment of an infectious disease by administering to a subject, preferably a human subject, a benzo[b]azepine TLR agonist formulation of the present invention, which contains a cyclodextrin. Preferably, the infectious disease is caused by a virus. In a particular embodiment, the virus is hepatitis C virus (HCV or HepC).

In certain embodiments of the methods for treating cancer or infectious disease, the benzo[b]azepine TLR agonist is administered to the subject at a dose of about 0.02 to 10 mg/kg or about 0.04 to 5 mg/kg body weight of the subject. In certain embodiments, the benzo[b]azepine TLR agonist is administered at a dose of about 0.02 mg/kg, about 0.05 mg/kg, about 1 mg/kg, about 2 mg/kg, or about 5 mg/kg. In certain further embodiments, the benzo[b]azepine TLR agonist formulation is administered to the subject on a weekly or biweekly basis.

The present invention also provides a pharmaceutical pack or kit comprising one or more containers filled with a liquid or lyophilized benzo[b]azepine TLR agonist formulation of the invention for the treatment of cancer or one or more symptoms thereof. Preferably, the formulation comprises about 1-30%, 5-15%, or 5-10% w/v of a cyclodextrin, preferably a β-cyclodextrin, and most preferably sulfobutylether β-cyclodextrin. In certain embodiments, the formulation comprises 2%, 5%, 10%, 15%, 20%, 25%, or 30% w/v of a cyclodextrin, preferably a β-cyclodextrin, and most preferably sulfobutylether β-cyclodextrin. In a particular embodiment, the formulation is an aqueous formulation of the benzo[b]azepine TLR agonist (1E, 4E)-2-amino-N,N-dipropyl-8-(4-(pyrrolidine-1-carbonyl)phenyl)-3H-benzo[b]azepine-4-carboxamide containing a β-cyclodextrin, preferably sulfobutylether β-cyclodextrin. In another embodiment, the formulation is a lyophilized formulation of (1E, 4E)-2-amino-N,N-dipropyl-8-(4-(pyrrolidine-1-carbonyl)phenyl)-3H-benzo[b]azepine-4-carboxamide containing a β-cyclodextrin, preferably sulfobutylether β-cyclodextrin. Preferably, the benzo[b]azepine TLR agonist is formulated at a concentration of at least 2 mg/ml and the formulation, whether aqueous or a reconstituted lyophilized formulation, is suitable for subcutaneous injection in a mammal, preferably a human.

The present invention also provides for a use of a formulation of a benzo[b]azepine TLR agonist, preferably a TLR7 or a TLR8 agonist in the manufacture of a medicament for treating cancer, an infectious disease, or atopic dermatitis in a subject. The cancer is selected from the group consisting of ovarian cancer, breast cancer, head and neck cancer, renal cancer, bladder cancer, hepatocellular cancer, and lymphoma.

In one embodiment, the TLR agonist is formulated at a concentration of at least 2 mg/ml. Moreover, the formulation is suitable for administration to the subject, where the subject is preferably a human, by injection and is by subcutaneous, intramuscular, or transdermal injection. In certain embodiments, the TLR agonist is administered to the subject at a dose of about 0.02 to 10 mg/kg, at a dose of about 0.04 to 5 mg/kg. In certain further embodiments, the benzo[b]azepine TLR agonist formulation is administered to the subject on a weekly or biweekly basis.

In a preferred embodiment, the benzo[b]azepine TLR agonist formulation is administered in combination with one or more additional treatment modalities, where the modalities are selected from a chemotherapeutic agent, a cytokine, an antibody, hormonal therapy, or radiation therapy. The present invention also provides methods for the treatment of infectious disease is caused by a virus, where the virus is a hepatitis virus.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

5. DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

The present invention provides stable formulations of benzo[b]azepine TLR agonists and methods of using the same. The benzo[b]azepine TLR agonists of the invention are preferably TLR7 or TLR8 agonists, or have agonist activity for both TLR7 and TLR8. Benzo[b]azepine TLR agonists which can be formulated according to the present invention are described in PCT International Application No. PCT/US2006/032098, filed Aug. 17, 2006. In a preferred embodiment, the benzo[b]azepine TLR agonist is (1E, 4E)-2-amino-N,N-dipropyl-8-(4-(pyrrolidine-1-carbonyl)phenyl)-3H-benzo[b]azepine-4-carboxamide and pharmaceutically acceptable salts thereof. The formulations of the present invention are suitable for use in methods for the treatment of human diseases such as cancer and infectious diseases as described herein.

TLR Agonists of the Invention

Benzo[b]azepine TLR agonists which can be formulated according to the present invention are described in PCT International Application No. PCT/US2006/032098, filed Aug. 17, 2006, published as WO 2007/024612 on Mar. 1, 2007, the contents of which are incorporated herein in their entirety. In a preferred embodiment, the benzo[b]azepine TLR agonist is (1E, 4E)-2-amino-N,N-dipropyl-8-(4-(pyrrolidine-1-carbonyl)phenyl)-3H-benzo[b]azepine-4-carboxamide and pharmaceutically acceptable salts thereof.

Preferably, the benzo[b]azepine TLR agonists of the present invention are compounds of Formula I:

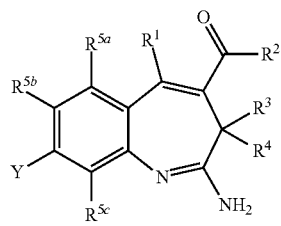

I and metabolites, solvates, tautomers, and pharmaceutically acceptable salts and
prodrugs thereof, wherein:

Y is $CF_2CF_3$, $CF_2CF_2R^6$, or an, aryl or heteroaryl ring, wherein said aryl and heteroaryl rings are substituted with one or more groups independently selected from alkenyl, alkynyl, Br, CN, OH, $NR^6R^7$, $C(=O)R^8$, $NR^6SO_2R^7$, $(C_1-C_6$ alkyl)amino, $R^6OC(=O)CH=CH_2—$, $SR^6$ and $SO_2R^6$, and wherein said aryl and heteroaryl rings are optionally further substituted with one or more groups independently selected from F, Cl, $CF_3$, $CF_3O—$, $HCF_2O—$, alkyl, heteroalkyl and ArO—;

$R^1$, $R^3$ and $R^4$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1-C_6$ alkyl)amino, $CH_3OCH_2O—$, $R^6OC(=O)CH=CH_2—$, $NR^6SO_2R^7$, $SR^6$, and $SO_2R^6$, or $R^3$ and $R^4$ together with the atom to which they are attached form a saturated or partially unsaturated carbocyclic ring, wherein said carbocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1-C_6$ alkyl)amino, $CH_3OCH_2O—$, $R^6OC(=O)CH=CH_2—$, $NR^6SO_2R^7$, $SR^6$, and $SO_2R^6$;

$R^2$ and $R^8$ are independently selected from H, $OR^6$, $NR^6R^7$, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1-C_6$ alkyl)amino, $CH_3OCH_2O—$, $R^6OC(=O)CH=CH_2—$, $NR^6SO_2R^7$, $SR^6$, and $SO_2R^6$; $R^{5a}$, $R^{5b}$, and $R^{5C}$ are independently H, F, Cl, Br, I, OMe, $CH_3$, $CH_2F$, $CHF_2$ or CF3;

and $R^6$ and $R^7$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6_R{}^7$, $C(=O)R^6$, $C(=O)OR^6$, $OC(=O)R^6$, $C(=O)NR^6R^7$, $(C_1-C_6$ alkyl)amino, $CH_3OCH_2O—$, $R^6OC(=O)CH=CH_2—$, $NR^6SO_2R^7$, $SR^6$, and $SO_2R^6$, or $R^6$ and $R^7$ together with the atom to which they are attached form a saturated or partially unsaturated heterocyclic ring, wherein said heterocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1-C_6$ alkyl)amino, $CH_3OCH_2O—$, $R^6OC(=O)CH=CH_2—$, $NR^6SO_2R^7$, $SR^6$, and $SO_2R^6$.

In certain embodiments, $R^1$, $R^3$, and $R^4$ are each hydrogen.

In certain embodiments, $R^{5a}$, $R^{5b}$, and $R^{5C}$ are each hydrogen.

In certain embodiments of the compound of Formula I, $R^2$ is $OR^6$. In certain embodiments, $R^6$ is alkyl, such as (1-4C) alkyl. In particular embodiments, $R^6$ is ethyl.

In certain embodiments of the compound of Formula I, $R^2$ is $NR^6R^7$. In certain embodiments, $R^6$ and $R^7$ are independently H, alkyl, such as (1-6C)alkyl, or heteroalkyl, such as (1-4C)alkoxy(2-4C)alkyl. In particular embodiments, $R^6$ and $R^7$ are independently H, ethyl, propyl, or $CH_2CH_2OCH_3$.

In certain embodiments of the compound of Formula I, Y is aryl, such as phenyl. In certain embodiments, said aryl is substituted with $C(=O)R^8$, such as in para-$R^8C(=O)$phenyl. In certain embodiments, $R^8$ is $OR^6$, $NR^6R^7$ or heterocycloalkyl. In certain embodiments, $R^6$ and $R^7$ are independently H or alkyl, such as (1-6C)alkyl. In certain other embodiments, $R^6$ and $R^7$ together with the nitrogen atom to which they are attached form a 4-6 membered azacycloalkyl ring, such as pyrrolidinyl. In particular embodiments, Y is

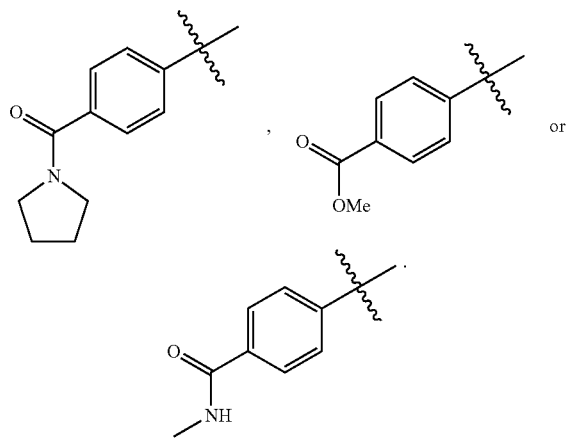

In certain embodiments of said compound of Formula I, Y is $CF_2CF_3$.

In specific embodiments, the benzo[b]azepine TLR agonist is selected from among the following compounds:

(1E, 4E)-ethyl 2-amino-8-(perfluoroethyl)-3H-benzo[b]azepine-4-carboxylate;
(1E, 4E)-2-amino-N,N-bis(2-methoxyethyl)-8-(perfluoroethyl)-3H-benzo[b]azepine-4-carboxamide;
(1E, 4E)-2-amino-N,N-diethyl-8-(perfluoroethyl)-3H-benzo[b]azepine-4-carboxamide;
(1E, 4E)-2-amino-8-(perfluoroethyl)-N,N-dipropyl-3H-benzo[b]azepine-4-carboxamide;
(1E, 4E)-2-amino-N-ethyl-8-(perfluoroethyl)-3H-benzo[b]azepine-4-carboxamide;
(1E, 4E)-2-amino-8-(perfluoroethyl)-N-propyl-3H-benzo[b]azepine-4-carboxamide;
(1E, 4E)-ethyl 2-amino-8-(pyrrolidine-1-carbonyl)-3H-benzo[b]azepine-4-carboxylate;
(1E, 4E)-ethyl 2-amino-8-(4-(methoxycarbonyl)phenyl)-3H-benzo[b]azepine-4-carboxylate;
(1E, 4E)-ethyl 2-amino-8-(4-(methylcarbamoyl)phenyl)-3H-benzo[b]azepine-4-carboxylate;
(1E, 4E)-2-amino-N,N-dipropyl-8-(4-(pyrrolidine-1-carbonyl)phenyl)-3H-benzo[b]azepine-4-carboxamide;

and pharmaceutically acceptable salts thereof.

5.1 Formulations

The present invention provides stable formulations of the benzo[b]azepine TLR agonists described in Section 5.1. The formulations of the invention are preferably suitable for pharmaceutical uses as described in Sections 5.3. Most preferably, the formulations are suitable for subcutaneous administration to a subject, preferably a human subject, but can be for administration by other means as described in Section 5.4.

The benzo[b]azepine TLR agonist formulations of the present invention comprise one or more pharmaceutically acceptable excipients. The term excipient as used herein broadly refers to a biologically inactive substance used in combination with the active agents of the formulation. An excipient can be used, for example, as a solubilizing agent, a stabilizing agent, a diluent, an inert carrier, a preservative, a binder, a disintegrant, a coating agent, a flavoring agent, or a coloring agent. Preferably, at least one excipient is chosen to provide one or more beneficial physical properties to the formulation, such as increased stability and/or solubility of the active agent(s). A benzo[b]azepine TLR agonist as described herein is the primary active agent in the formulations of the present invention. However, a benzo[b]azepine TLR agonist may be formulated with other active agents, e.g., other TLR agonists, anti-cancer agents or anti-viral agents, as described herein.

A "pharmaceutically acceptable" excipient is one that has been approved by a state or federal regulatory agency for use in animals, and preferably for use in humans, or is listed in the U.S. Pharmacopia, the European Pharmacopia or another generally recognized pharmacopia for use in animals, and preferably for use in humans.

Examples of excipients include certain inert proteins such as albumins; hydrophilic polymers such as polyvinylpyrrolidone; amino acids such as aspartic acid (which may alternatively be referred to as aspartate), glutamic acid (which may alternatively be referred to as glutamate), lysine, arginine, glycine, and histidine; fatty acids and phospholipids such as alkyl sulfonates and caprylate; surfactants such as sodium dodecyl sulphate and polysorbate; nonionic surfactants such as such as TWEEN®, PLURONICS®, or polyethylene glycol (PEG); carbohydrates such as glucose, sucrose, mannose, maltose, trehalose, and dextrins, including cyclodextrins; polyols such as mannitol and sorbitol; chelating agents such as EDTA; and salt-forming counter-ions such as sodium.

The formulations of the present invention preferably contain a cyclodextrin which increases the aqueous solubility of the TLR agonist. Cyclodextrins are crystalline, nonhygroscopic cyclic oligomers of α-D-glucopyranose. As a result of a lack of rotation about the bonds connecting the glucopyranose units, the cyclodextrins are not cylindrical, but toroidal in shape. Because of this restricted rotation they have a rigid structure with a central cavity whose size varies according to the number of glucopyranose units in the molecule. The three most common cyclodextrins are α-cyclodextrin, β-cyclodextrin and γ-cyclodextrin, which consist of six, seven, or eight glucopyranose units, respectively. Due to the arrangement of hydroxyl groups within the cyclodextrin molecule and the shape of the molecule, the internal surface of the cavity is hydrophobic, while the outside surface is hydrophilic. The primary hydroxyl groups are located on the narrower (inner) side of the toroidal molecule, while the secondary hydroxyl groups are located on the wider (outer) edge. This arrangement permits the cyclodextrins to accommodate a wide variety of small hydrophobic molecules within the hydrophobic cavity by forming an inclusion complex.

Suitable cyclodextrins for use in the formulations of the invention are known in the art. For example, TRAPPSOL™ and other cyclodextrins are made by CTD, Inc. (High Springs, Fla.), and CAPTISOL® (sulfobutylether β-cyclodextrin) is present in commercially available injectables such as ABILIFY IM™, GEODON, and VFEND IV. Preferably, CAPTISOL® is used in the formulations of the present invention.

In certain embodiments, the formulation comprises 1-30%, 2-12%, 5-15%, 15-20%, 20-25%, or 25-30% w/v of a cyclodextrin, preferably a β-cyclodextrin, and most preferably sulfobutylether β-cyclodextrin. In other embodiments, the formulation comprises 2%, 4%, 6%, 8%, 10%, 12%, or 15% w/v of a cyclodextrin, preferably a β-cyclodextrin, and most preferably sulfobutylether β-cyclodextrin. In other embodiments, the formulation comprises 20%, 25%, or 30% w/v of a cyclodextrin, preferably a β-cyclodextrin, and most preferably sulfobutylether β-cyclodextrin. In a particular embodiment, the formulation comprises 5%, 15%, 25%, or 30% of a cyclodextrin, preferably a β-cyclodextrin, and most preferably sulfobutylether β-cyclodextrin.

Although cyclodextrins are the preferred solubilizing agents, other water-solubilizing agents may be used.

Examples of other such agents include Poloxamer, Povidone K17, Povidone K12, Tween 80, ethanol, Cremophor/ethanol, polyethylene glycol 300, polyethylene glycol 400, and propylene glycol. In preferred embodiments, the formulations of the invention contain less than 10% v/v of such agents. In certain embodiments, oil-based solubilizing agents such as lipiodol and peanut oil, are used.

The formulations of the present invention may also contain pharmaceutically acceptable salts, buffering agents, or preservatives. Examples of such salts include those prepared from the following acids: hydrochloric, hydrobromic, sulfuric, nitric, phosphoric, maleic, acetic, salicylic, citric, boric, formic, malonic, succinic, and the like. Such salts can also be prepared as alkaline metal or alkaline earth salts, such as sodium, potassium or calcium salts. Examples of buffering agents include phosphate, citrate, acetate, and 2-(N-morpholino)ethanesulfonic acid (MES). Examples of preservatives include antioxidants such as vitamin A, vitamin E, vitamin C, retinyl palmitate, and selenium; the amino acids cysteine and methionine; citric acid and sodium citrate; and synthetic preservatives such as thimerosal, and alkyl parabens, including for example, methyl paraben and propyl paraben. Other preservatives include octadecyldimethylbenzyl ammonium chloride, hexamethonium chloride, benzalkonium chloride, benzethonium chloride, phenol, butyl or benzyl alcohol, chlorobutanol, catechol, resorcinol, cyclohexanol, 3-pentanol, and m-cresol.

In certain embodiments, the formulations of the invention may be prepared as a liquid or in a solid form such as a powder, tablet, pill or capsule. Liquid formulations may take such forms as suspensions, solutions or emulsions in oily or aqueous vehicles, and may contain formulatory agents such as suspending, stabilizing and/or dispersing agents. In one embodiment, the formulation is an aqueous solution. In another embodiment, the final formulation is lyophilized. In other embodiments, the formulation comprises a colloidal drug delivery system. Such drug delivery systems include, for example, liposomes, albumin microspheres, microemulsions, nano-particles and nanocapsules.

In one embodiment, the benzo[b]azepine TLR agonist formulation is a liquid or lyophilized formulation suitable for injection in a mammal, preferably a human. In one embodiment, the formulation is sterile. In another embodiment, the formulation is a sterile lyophilized formulation which is suitable for injection upon reconstitution with an amount of an aqueous carrier. In one embodiment, the liquid or lyophilized formulation is prepared as a unit dosage form as described below. The formulations may or may not contain an added preservative.

In certain embodiments, the formulations further comprise one or more adjuvants. Examples of suitable adjuvants include potentiators of the immune response such as microbial derivatives (e.g., bacterial products, toxins such as cholera toxin and heat labile toxin from E. coli, lipids, lipoproteins, nucleic acids, peptidoglycans, carbohydrates, peptides), cells, cytokines, (e.g., dendritic cells, IL-12, and GM-CSF), hormones, and small molecules. Adjuvants contemplated include, but are not limited to, oil-based adjuvants (e.g., Freund's adjuvant), CpG oligonucleotides, aluminum salt adjuvants, calcium salt adjuvants, emulsions and surfactant-based formulations (e.g., MF59, ASO2, montanide, ISA-51, ISA-720, and QA21).

According to certain embodiments, the benzo[b]azepine TLR agonist is formulated at a concentration of from about 0.5 to about 50 mg/ml. In some embodiments, the benzo[b]azepine TLR agonist is formulated at a concentration of from about 1 mg/ml to about 5 mg/ml, from about 1 mg/ml to about 10 mg/ml, from about 1 mg/ml to about 20 mg/ml, or from about 1 mg/ml to about 30 mg/ml. In other embodiments, the benzo[b]azepine TLR agonist is formulated at a concentration of from about 0.5 mg/ml to about 1 mg/ml, from about 0.5 mg/ml to about 2 mg/ml, or from about 0.5 mg/ml to about 5 mg/ml. In certain embodiments, the benzo[b]azepine TLR agonist is formulated at a concentration of between 0.5 and 10 mg/ml, between 0.5 and 5 mg/ml, or between 1 and 5 mg/ml. In other embodiments, the benzo[b]azepine TLR agonist is formulated at a concentration of between 10-20 mg/ml, 20-30 mg/ml, or between 30-50 mg/ml. In specific embodiments, the benzo[b]azepine TLR agonist is formulated at a concentration of about 1 mg/ml, about 2 mg/ml, about 4 mg/ml, about 5 mg/ml, about 6 mg/ml, about 8 mg/ml, about 10 mg/ml, about 15 mg/ml, about 20 mg/ml, about 25 mg/ml, about 30 mg/ml, or about 40 mg/ml.

In certain embodiments, the pH of the benzo[b]azepine TLR agonist formulation is acidic (meaning less than 7). Preferably, the pH of the benzo[b]azepine TLR agonist formulation is from about 5.0 to about 7, preferably from about 5.5 to about 6.5. In a particular preferred embodiment, the pH is 6.5.

In certain embodiments, the benzo[b]azepine TLR agonist is formulated in polyethylene glycol or propylene glycol at a concentration of at least 5 mg/ml, at least 8 mg/ml, or at least 9 mg/ml. In accordance with one aspect of these embodiments, the polyethylene glycol or propylene glycol is present in solution at between 10-20% v/v. In accordance with another aspect of these embodiments, both polyethylene glycol and propylene glycol are present in solution, each at 7.5%, 10%, or 15% v/v.

In certain embodiments, the benzo[b]azepine TLR agonist is formulated in a cyclodextrin, preferably β-cyclodextrin, and most preferably sulfobutylether β-cyclodextrin at a concentration of from about 0.5 mg/ml to about 50 mg/ml. In accordance with one aspect of these embodiments, the cyclodextrin, preferably a β-cyclodextrin, is about 1-30% w/v. In specific aspects of these embodiments, the cyclodextrin, preferably a β-cyclodextrin, is about 1% w/v, about 2% w/v, about 5% w/v, about 10% w/v, about 15% w/v, about 20% w/v, about 25% w/v, or about 30% w/v.

In embodiments where the formulation is an emulsion, suitable emulsifiers or emulsifying agents include any pharmaceutically acceptable emulsifier, preferably phospholipids extracted from egg yolk or soy bean, synthetic phosphatidyl cholines or purified phosphatidyl cholines from vegetable origin. Hydrogenated derivatives can also be used, such as phosphatidylcholine hydrogenated (egg) and phosphatidylcholine hydrogenated (soya). Emulsifiers may also be non-ionic surfactants such as poloxamers (for example Poloxamer 188 and 407), poloxamines, polyoxyethylene stearates, polyoxyethylene sorbitan fatty acid esters or sorbitan fatty acid esters. Ionic surfactants may also be used such as cholic acid and deoxycholic acid or surface active derivatives or salts thereof. The emulsifier can also be a mixture of one or more of the above ingredients. The emulsion may additionally contain other ingredients such as buffers, stabilizers and other lipids.

The formulations of the present invention can optionally be prepared as unit dosage forms. "Unit dosage form" refers to physically discrete units suitable for the intended use, i.e., as a single administration to the subject to be treated. Each unit contains a predetermined quantity of the active agent(s) formulated with the appropriate pharmaceutically acceptable excipient(s). For example, a unit dosage per vial may contain a certain volume, such as 1 ml, 2 ml, 3 ml, 4 ml, 5 ml, 6 ml, 7 ml, 8 ml, 9 ml, 10 ml, 15 ml, or 20 ml, having a particular concentration of the active agent. A dosage unit may comprise a single active agent, i.e., a benzo[b]azepine TLR agonist as described herein, its derivatives and analogs, or mixtures thereof with other active agents for use in combination therapies. In preferred embodiments, the unit dosage form comprises about 15 mg/ml to about 40 mg/ml of a benzo[b] azepine TLR agonist. The formulations are optionally contained in unit-dose or multi-dose containers, for example, in sealed ampules or vials, and may be in a lyophilized condition. Extemporaneous injection solutions and suspensions may be prepared from sterile powders, granules and tablets according to art-recognized methods. Examples of unit dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for subcutaneous administration to a subject; and sterile solids (e.g., crystalline or amorphous solids) that can be reconstituted to provide liquid dosage forms suitable for subcutaneous administration to a subject.

Sustained-release preparations may also be prepared. Sustained-release preparations include semipermeable matrices of solid hydrophobic polymers containing the benzo[b] azepine TLR agonist, which matrices are in the form of shaped articles, e.g., films, or microcapsules. Examples of such matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release molecules for shorter time periods.

In certain preferred embodiments, a benzo[b]azepine TLR agonist formulation of the invention comprises 1-30% w/v of a β-cyclodextrin, most preferably sulfobutylether β-cyclodextrim, and one or more of the following benzo[b]azepine TLR agonists at a concentration of about 2 mg/ml, about 5 mg/ml, about 10 mg/ml, or about 15 mg/ml, in a form suitable for injection to a mammal, preferably a human: (1E, 4E)-ethyl 2-amino-8-(perfluoroethyl)-3H-benzo[b]azepine-4-carboxylate; (1E, 4E)-2-amino-N,N-bis(2-methoxyethyl)-8-(perfluoroethyl)-3H-benzo[b]azepine-4-carboxamide; (1E, 4E)-2-amino-N,N-diethyl-8-(perfluoroethyl)-3H-benzo[b] azepine-4-carboxamide; (1E, 4E)-2-amino-8-(perfluoroethyl)-N,N-dipropyl-3H-benzo[b]azepine-4-carboxamide; (1E, 4E)-2-amino-N-ethyl-8-(perfluoroethyl)-3H-benzo[b] azepine-4-carboxamide; (1E, 4E)-2-amino-8-(perfluoroethyl)-N-propyl-3H-benzo[b]azepine-4-carboxamide; (1E, 4E)-ethyl 2-amino-8-(pyrrolidine-1-carbonyl)-3H-benzo[b] azepine-4-carboxylate; (1E, 4E)-ethyl 2-amino-8-(4-(methoxycarbonyl)phenyl)-3H-benzo[b]azepine-4-carboxylate; (1E, 4E)-ethyl 2-amino-8-(4-(methylcarbamoyl)phenyl)-3H-benzo[b]azepine-4-carboxylate; (1E, 4E)-2-amino-N,N-dipropyl-8-(4-(pyrrolidine-1-carbonyl)phenyl)-3H-benzo[b] azepine-4-carboxamide; and pharmaceutically acceptable salts thereof.

Additional information with regard to the methods of making the compositions and formulations and the ingredients comprising the compositions and formulations in accordance with the present invention can be found in standard references in the field, such as for example, "Remington's Pharmaceutical Sciences," Mack Publishing Co., Easton, Pa.

5.1.1 Stability

The formulations of the present invention provide for the chemical stability of the formulated benzo[b]azepine TLR agonist. "Stability" and "stable" in the context of the present invention refers to the resistance of the benzo[b]azepine TLR agonist to chemical degradation under given manufacturing, preparation, transportation and storage conditions. The "stable" formulations of the invention also preferably retain at least 80%, 85%, 90%, 95%, 98%, 99%, or 99.5% of the biological activity of a standard or reference preparation of the benzo[b]azepine TLR agonist under given manufacturing, preparation, transportation, and/or storage conditions. Biological activity refers to the ability of the benzo[b]azepine TLR agonist to activate TLR signaling, preferably TLR7 and/or TLR8 signaling, and most preferably TLR8 signaling. In this context, biological activity can be measured using any art-recognized method for detecting TLR signaling. For example, such methods include assays for the detection of TLR-dependent intracellular signal transduction molecules, such as nuclear factor kappa beta (NFkB). Such assays include, e.g., reporter gene assays conducted in cells that stably express one or more TLR genes, preferably TLR 7 and/or TLR8 genes. Other methods include assays for the detection of cytokines which are released by TLR-containing cells of the immune system when TLR signaling is activated. For example, assays for the detection of tumor necrosis factor alpha (TNFa) or interferon alpha (IFNα) in the supernatant of cultured cells are known to the skilled person and are commercially available (see e.g., R&D Systems, Minneapolis, Minn.).

The "stable" formulations of the invention also preferably retain at least 90%, 95%, 98%, 99%, or 99.5% of a starting or reference amount of the benzo[b]azepine TLR agonist under given manufacturing, preparation, transportation, and/or storage conditions. The amount of benzo[b]azepine TLR agonist can be determined using any art-recognized method. For example, benzo[b]azepine TLR agonist concentration can be determined using routine methods such as UV-Vis spectrophotometry and high pressure liquid chromatography (HPLC).

In certain embodiments, the present formulations are stable at temperatures ranging from about 20 to 30° C. for at least 1 week, at least 2 weeks, at least 3 weeks, at least 4 weeks, at least 5 weeks, at least 6 weeks, or at least 7 weeks. In other embodiments, the formulations are stable at temperatures ranging from about 20 to 30° C. for at least 1 month, at least 2 months, at least 3 months, at least 4 months, at least 5 months, at least 6 months, at least 7 months, at least 8 months, at least 9 months, at least 10 months, at least 11 months, or at least 12 months. In one embodiment, the formulation is stable for at least 2 months at 20-25° C.

In other embodiments, the present formulations are stable at temperatures ranging from about 2 to 8° C. for at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months. In one embodiment, the formulation is stable for at least 2 months at 2 to 8° C.

In other embodiments, the present formulations are stable at temperatures of about −20° C. for at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months. In one embodiment, the formulation is stable for at least 6-12 months at 20° C.

In a particular embodiment, a benzo[b]azepine TLR agonist formulation of the invention is stable at temperatures of about 20-30° C. at concentrations up to 40 mg/ml for at least 2 weeks, preferably for at least 4 weeks, and most preferably for at least 8 weeks. In another embodiment, the formulation is stable at temperatures from about 2-8° C. at concentrations up to 40 mg/ml for at least 4 weeks, preferably for at least 8 weeks, and most preferably for at least 12 weeks. In a another embodiment, the formulation is stable at temperatures of about −20° C. at concentrations up to 40 mg/ml for at least 8 weeks, preferably for at least 12 weeks, and most preferably for at least 16 weeks.

5.2 Methods of Use

The benzo[b]azepine TLR agonist formulations of the present invention are useful in methods for the treatment of cancer or infectious diseases. Preferably, the benzo[b]azepine TLR agonist formulations are used in combination with one or more additional treatment modalities in a regiment for the treatment of cancer. In certain embodiments, the cancer is a solid tumor. In one embodiment, the cancer is selected from the group consisting of ovarian cancer, breast cancer, head and neck cancer, renal cancer, bladder cancer, hepatocellular cancer, and lymphoma. In a particular embodiment, the cancer is a lymphoma. In one embodiment, the lymphoma is non-Hodgkins lymphoma. The benzo[b]azepine TLR agonist formulations of the present invention are also useful in other methods including methods for the treatment of certain skin conditions or diseases, such as atopic dermatitis, methods for the treatment of infectious diseases, preferably viral diseases, and for use as adjuvants in vaccines formulated for use in cancer therapy or for the treatment or prevention of infectious diseases, preferably viral diseases. In one embodiment, the infectious disease is a viral disease and the virus is a hepatitis virus, preferably hepatitis C virus (HCV or HepC). The benzo[b]azepine TLR agonist formulations of the invention can be used either alone or in combination with one or more other treatment modalities as described in Section 5.3.1.

5.2.1 Combination Therapy

Combination therapy encompasses, in addition to the administration of a benzo[b]azepine TLR agonist formulation of the invention, the adjunctive use of one or more modalities that aid in the prevention or treatment of cancer. Such modalities include, but are not limited to, chemotherapeutic agents, immunotherapeutics, anti-angiogenic agents, cytokines, hormones, antibodies, polynucleotides, radiation and photodynamic therapeutic agents. In specific embodiments, combination therapy can be used to prevent the recurrence of cancer, inhibit metastasis, or inhibit the growth and/or spread of cancer or metastasis. As used herein, "in combination with" means that the benzo[b]azepine TLR agonist formulation of the invention is administered as part of a treatment regimen that comprises one or more additional treatment modalities as described in more detail in the following sections.

In certain embodiments, the benzo[b]azepine TLR agonist is administered prior to, concurrently with, or subsequent to the administration of the one or more other modalities. In one embodiment the benzo[b]azepine TLR agonist is formulated with one or more other modalities. In another embodiment, the one or more other modalities is administered in a separate pharmaceutical composition. In accordance with this embodiment, the one or more other modalities may be administered to a subject by the same or different routes of administration as those used to administer the benzo[b]azepine TLR agonist.

5.2.1.1 Combination with Anti-cancer Agents

In certain embodiments, the formulation comprising a benzo[b]azepine TLR agonist of the invention is administered in combination with one or more anti-cancer agents, preferably a chemotherapeutic agent. Such chemotherapeutic agents include, but are not limited to, the following groups of compounds: cytotoxic antibiotics, antimetabolities, anti-mitotic agents, alkylating agents, platinum compounds, arsenic compounds, DNA topoisomerase inhibitors, taxanes, nucleoside analogues, plant alkaloids, and toxins; and synthetic derivatives thereof. The following are non-limiting examples of particular compounds within these groups. Alkylating agents include nitrogen mustards such as cyclophosphamide, ifosfamide, trofosfamide, and chlorambucil; nitrosoureas such as carmustine (BCNU) and lomustine (CCNU); alkylsulphonates such as busulfan and treosulfan; and triazenes such as dacarbazine. Platinum containing compounds include cisplatin, carboplatin, aroplatin, and oxaliplatin. Plant alkaloids include vinca alkaloids such as vincristine, vinblastine, vindesine, and vinorelbine; and taxoids such as paclitaxel and docetaxol. DNA topoisomerase inhibitors include epipodophyllins such as etoposide, teniposide, topotecan, 9-aminocamptothecin, camptothecin, and crisnatol; and mitomycins such as mitomycin C. Anti-folates include DHFR inhibitors such as methotrexate and trimetrexate; IMP dehydrogenase inhibitors such as mycophenolic acid, tiazofurin, ribavirin, hydroxyurea and EICAR; and ribonuclotide reductase inhibitors such as deferoxamine. Pyrimidine analogs include uracil analogs such as 5-fluorouracil, floxuridine, doxifluridine, and ratitrexed; and cytosine analogs such as cytarabine (ara C), cytosine arabinoside, and fludarabine. Purine analogs include mercaptopurine and thioguanine. DNA antimetabolites include 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, inosine glycodialdehyde, macebecin II, and pyrazoloimidazole. Antimitotic agents include allocolchicine, halichondrin B, colchicine, colchicine derivative, dolstatin 10, maytansine, rhizoxin, thiocolchicine, and trityl cysteine.

Other examples of chemotherapeutic agents for use with the benzo[b]azepine TLR agonist formulations of the invention include isoprenylation inhibitors; dopaminergic neurotoxins such as 1-methyl-4-phenylpyridinium ion; cell cycle inhibitors such as staurosporine; actinomycins such as actinomycin D and dactinomycin; bleomycins such as bleomycin A2, bleomycin B2, and peplomycin; anthracyclines such as daunorubicin, doxorubicin (adriamycin), idarubicin, epirubicin, pirarubicin, zorubicin, and mitoxantrone; MDR inhibitors such as verapamil; and $Ca^{2+}$ ATPase inhibitors such as thapsigargin.

Compositions comprising one or more chemotherapeutic agents (e.g., FLAG, CHOP) are also contemplated for use in combination with the benzo[b]azepine TLR agonist formulations of the invention. FLAG comprises fludarabine, cytosine arabinoside (Ara-C) and G-CSF. CHOP comprises cyclophosphamide, vincristine, doxorubicin, and prednisone. Each of the foregoing lists is illustrative, and is not intended to be limiting.

In one embodiment, the benzo[b]azepine TLR agonist formulation of the invention is administered in combination with one or more of the following: IFNα, IL-2, Dacarbazine (Bayer), Temozolomide (Schering), Tamoxifen (AZ), Carmustine (BMS), Melphalan (GSK), Procarbazine (Sigma-Tau), Vinblastine, carboplatin, cisplatin, taxol, cyclophosphamide, doxorubin, Rituxan (Genentech/Roche), Herceptin (Genentech/Roche), Gleevec, Iressa (AZ), Avastin (Genentech/Roche), or Tarceva (Genentech/Roche).

In another embodiment, the benzo[b]azepine TLR agonist formulation of the invention is administered in combination with one or more of the following: an enediyne such as calicheamicin and esperamicin; duocarmycin, methotrexate, doxorubicin, melphalan, chlorambucil, Ara-C, vindesine, mitomycin C, cis-platinum, etoposide, bleomycin, and 5-fluorouracil.

Suitable toxins and chemotherapeutic agents that can be used in combination with the benzo[b]azepine TLR agonist formulations of this invention are described in Remington's Pharmaceutical Sciences, 19th Ed. (Mack Publishing Co. 1995), and in Goodman and Gilman's the Pharmacological Basis of Therapeutics, 7th Ed. (MacMillan Publishing Co. 1985). Other suitable toxins and/or chemotherapeutic agents are known to those of skill in the art.

Further examples of anti-cancer agents that can be used in combination with the benzo[b]azepine TLR agonist formulations of this invention include without limitation the following: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be used include, but are not limited to: 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat;

imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

5.2.1.2 Combination with Radiation Therapy

In another embodiment, the benzo[b]azepine TLR agonist formulations of the invention are administered in conjunction with a regimen of radiation therapy for the treatment of cancer. The methods encompass regimens comprising external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. Any suitable cytotoxic radionuclide or therapeutic isotope may be used in the regimen of radiation therapy. In certain embodiments, the isotope is an alpha-emitting isotope such as $^{225}$Ac, $^{224}$Ac, $^{211}$At, $^{212}$Bi, $^{213}$Bi, $^{212}$Pb, $^{224}$Ra, or $^{223}$Ra. In other embodiments, the cytotoxic radionuclide is a beta-emitting isotope such as $^{186}$Re, $^{188}$Re, $^{90}$Y, $^{131}$I, $^{67}$Cu, $^{177}$Lu, $^{153}$Sm, $^{166}$Ho, or $^{64}$Cu. In some embodiments, cytotoxic radionuclide is an isotope that emits Auger and low energy electrons such as $^{125}$I, $^{123}$I or $^{77}$Br. In other embodiments the isotope is $^{198}$Au, $^{32}$P, and the like.

In certain embodiments, the amount of the radionuclide administered to the subject is between about 0.001 mCi/kg and about 10 mCi/kg. In some embodiments, the amount of the radionuclide administered to the subject is between about 0.1 mCi/kg and about 1.0 mCi/kg. In other embodiments, the amount of the radionuclide administered to the subject is between about 0.005 mCi/kg and 0.1 mCi/kg.

5.2.1.3 Combination with Therapeutic Antibodies

In another embodiment, a benzo[b]azepine TLR agonist formulation of the invention is administered in combination with one or more immunotherapeutic agents, such as an antibody or a vaccines. In some embodiments, the antibodies have in vivo therapeutic and/or prophylactic uses against cancer. In some embodiments, the antibodies can be used for treatment and/or prevention of infectious disease.

Non-limiting examples of therapeutic and prophylactic antibodies that can be used in combination with a benzo[b]azepine TLR agonist formulation of the invention include MDX-010 (Medarex, NJ) which is a humanized anti-CTLA-4 antibody currently in clinic for the treatment of prostate cancer; SYNAGIS® (MedImmune, MD) which is a humanized anti-respiratory syncytial virus (RSV) monoclonal antibody for the treatment of RSV infection; and HERCEPTIN® (Trastuzumab) (Genentech, CA) which is a humanized anti-HER2 monoclonal antibody for the treatment of metastatic breast cancer. Other examples are humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti-Hepatitis B virus antibody (Protein Design Lab/Novartis); PROTOVIR™ which is a humanized anti-CMV IgG1 antibody (Protein Design Lab/Novartis); MAK-195 (SEGARD) which is a murine anti-TNF-α F(ab')$_2$ (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti-CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genentech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/Norvartis/Tanox Biosystems); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab')$_2$ (Pasteur-Merieux/Immunotech); CAT-152 is a human anti-TGF-β$_2$ antibody (Cambridge Ab Tech); and Corsevin M is a chimeric anti-Factor VII antibody (Centocor). The above-listed immunoreactive reagents, as well as any other immunoreactive reagents, may be administered according to any regimen known to those of skill in the art, including the regimens recommended by the suppliers of the immunoreactive reagents.

5.2.1.4 Combination with Other Therapeutic Agents

In addition to anti-cancer agents and therapeutic antibodies, the benzo[b]azepine TLR agonist formulations of the invention can be administered in combination with other therapeutic agents such as anti-angiogenic agents (e.g., in methods for the treatment of solid tumors and for the treatment and prevention of metastases) and anti-hormonal agents (particularly in methods for the treatment of hormone-dependent cancers such as breast cancer and prostate cancer).

In one embodiment, a benzo[b]azepine TLR agonist formulation of the invention is administered in combination with one or more anti-angiogenic agents. Such agents include, without limitation, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a β-amino acid peptide corresponding to a fragment of platelet factor-4 (Maione et al., 1990, Cancer Res. 51:2077-2083), a 14-amino acid peptide corresponding to a fragment of collagen I (Tolma et al., 1993, J. Cell Biol. 122:497-511), a 19 amino acid peptide corresponding to a fragment of Thrombospondin I (Tolsma et al., 1993, J. Cell Biol. 122:497-511), a 20-amino acid peptide corresponding to a fragment of SPARC (Sage et al., 1995, J. Cell. Biochem. 57:1329-1334), or any fragments, family members, or variants thereof, including pharmaceutically acceptable salts thereof.

Other peptides that inhibit angiogenesis and correspond to fragments of laminin, fibronectin, procollagen, and EGF have also been described (see, e.g., Cao, 1998, Prog Mol Subcell Biol. 20:161-176). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569-571; Hammes et al., 1996, Nature Medicine 2:529-533). Moreover, inhibition of the urokinase plasminogen activator receptor by receptor antagonists inhibits angiogenesis, tumor growth and metastasis (Min et al., 1996, Cancer Res. 56: 2428-33; Crowley et al., 1993, Proc Natl Acad Sci. 90:5021-25).

In another embodiment, a benzo[b]azepine TLR agonist formulation of the invention is used in association with a hormonal treatment modality. Such treatment modalities include the administration of hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), and antiandrogens (e.g., cyproterone acetate).

In another embodiment, a benzo[b]azepine TLR agonist formulation of the invention is used in association with a treatment modality that utilizes polynucleotide compounds, such as antisense polynucleotides, ribozymes, RNA interference molecules, triple helix polynucleotides and the like.

5.2.1.5 Combination with Immunoregulatory Agents

In certain embodiments, a benzo[b]azepine TLR agonist formulation of the invention is administered in combination with an immunoregulatory agent. In some embodiments, the benzo[b]azepine TLR agonist is formulated with the immunoregulatory agent. An "immunoregulatory agent" is a substance that suppresses, masks, or enhances the immune system of the subject to whom it is administered. Exemplary agents are those that suppress cytokine production, downregulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies; anti-tumor necrosis factor-α antibodies; anti-tumor necrosis factor-β antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain; streptokinase; TGF-β; streptodornase; FK506; RS-61443; deoxyspergualin; and rapamycin. Examples of cytokines include, but are not limited to lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-α; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleukins (ILs) such as IL-1, IL-1a, IL-2, IL-3, IL-4, IL-5, IL-6, IL-7, IL-8, IL-9, IL-1 I, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

In certain embodiments, the methods further include administering to the subject one or more immunomodulatory agents, preferably a cytokine. Preferred cytokines are selected from the group consisting of interleukin-1 (IL-1), IL-2, IL-3, IL-12, IL-15, IL-18, G-CSF, GM-CSF, thrombopoietin, and γ interferon.

5.2.1.6 Combination with Compounds that Enhance Monocyte or Macrophage Function

In certain embodiments, a compound that enhances monocyte or macrophage function (e.g., at least about 25%, 50%, 75%, 85%, 90%, 9% or more) can be used in conjunction with the benzo[b]azepine TLR agonist formulations of the invention. Such compounds are known in the art and include, without limitation, cytokines such as interleukins (e.g., IL-12), and interferons (e.g., alpha or gamma interferon).

In certain embodiments, the compound that enhances monocyte or macrophage function is formulated with the benzo[b]azepine TLR agonist and is thus administered concurrently with the benzo[b]azepine TLR agonist.

In other embodiments, the compound that enhances monocyte or macrophage function is administered separately from the benzo[b]azepine TLR agonist and can be administered concurrently (within a period of hours of each other), during the same course of therapy, or sequentially with the benzo[b]azepine TLR agonist. In such embodiments, the compound that enhances monocyte or macrophage function is preferably administered to a human subject. In one embodiment, the human subject has a blood leukocyte, monocyte, neutrophil, lymphocyte, and/or basophil count that is within the normal range for humans. Normal ranges for human blood leukocytes (total) is about 3.5-10.5 ($10^9$/L). Normal ranges for human blood neutrophils is about 1.7-7.0 ($10^9$/L), monocytes is about 0.3-0.9 ($10^9$/L), lymphocytes is about 0.9-2.9 ($10^9$/L), basophils is about 0-0.3 ($10^9$/L), and eosinophils is about 0.05-0.5 ($10^9$/L). In other embodiments, the human subject has a blood leukocyte count that is less than the normal range for humans, for example at least about 0.01, 0.05, 0.1, 0.2, 0.3, 0.4, 0.5, 0.6, 0.7, or 0.8 ($10^9$/L) leukocytes.

5.2.2 Target Cancers

In certain preferred embodiments, the type of cancer that is treated by the methods of the present invention is ovarian cancer, breast cancer, head and neck cancer, renal cancer, bladder cancer, hepatocellular cancer, or lymphoma. Other types of cancers that can be treated by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilms' tumor, cervical cancer, testicular tumor, lung carcinoma, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

5.2.3 Infectious Diseases and Agents

The benzo[b]azepine TLR agonist formulations of the present invention can be used in methods of treating or preventing an infectious disease in a subject, preferably a human subject. In certain embodiments, the method is a method for the treatment or prevention of an infectious disease caused by a virus, bacteria, fungi, protozoa, helminth, or parasite, including particular strains thereof.

In certain embodiments, a benzo[b]azepine TLR agonist formulation of the invention is used in a method of treating a viral disease caused by herpes viruses (HSV-1, HSV-2, VZV, EBV, CMV, HHV-6, HHV-8), influenza viruses (Flu A, B), hepatitis viruses (HepA, HepB, HepC, HepE), human immunodeficiency viruses (HIV-1, HIV-2), respiratory syncytial viruses, measles viruses, rhinoviruses, adenoviruses, SARS viruses, papillomaviruses, orthopoxviruses, or West Nile viruses. In a preferred embodiment, the benzo[b]azepine TLR agonist formulations of the invention are used in a method for the treatment of hepatitis, preferably hepatitis C (also referred to as HCV).

In certain embodiments, the benzo[b]azepine TLR agonist formulation is administered in combination with an anti-viral agent. Antiviral agents that can be used include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In one embodiment, the antiviral agent is a non-nucleoside reverse transcriptase inhibitor selected from the group consisting of delavirdine, efavirenz, and nevirapine. In one embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In one embodiment, the antiviral agent is a protease inhibitor selected from the group consisting of amprenavir, atazanavir, fosamprenav, indinavir, lopinavir, nelfinavir, ritonavir, and saquinavir. In one embodiment, the antiviral agent is a fusion inhibitor such as enfuvirtide.

Additional, non-limiting examples of antiviral agents for use in the methods of the invention include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscarnet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

Other examples of viruses encompassed by the methods of the invention include, without limitation, the following viruses: Retroviridae (e.g. human immunodeficiency viruses, such as HIV-1, also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola-like viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arenaviridae (hemorrhagic fever viruses); Reoviridae (e.g. reoviruses, orbiviurses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2), varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis, thought to be a defective satellite of hepatitis B virus), the agents of non-A, non-B hepatitis (class 1, internally transmitted; class 2, parenterally transmitted, i.e., Hepatitis C); Norwalk and related viruses, and astroviruses.

In other embodiments, a benzo[b]azepine TLR agonist formulation of the invention is used in a method of treating a disease caused by a bacterium. Non-limiting examples of bacteria encompassed by the methods of the invention include *Mycobacteria, Streptococcus, Staphylococcus, Pseudomonas, Salmonella, Neisseria*, and *Listeria*. Other examples of bacteria contemplated include, but are not limited to, Gram positive bacteria (e.g., *Listeria, Bacillus* such as *Bacillus anthracis, Erysipelothrix* species), Gram negative bacteria (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces and Clostridium* species), Gram positive and negative coccal bacteria, *Enterococcus* species, *Streptococcus* species, *Pneumococcus* species, *Staphylococcus* species, *Neisseria* species. Additional non-limiting examples of specific infectious bacteria include *Helicobacter pyloris, Borelia burgdorferi, Legionella pneumophilia, Mycobacteria avium, M. intracellulare, M. kansaii, M. gordonae, M. africanum, Staphylococcus aureus, Neisseria meningitidis, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneumoniae, Pasturella multocida, Fusobacterium nucleatum, Streptobacillus moniliformis, Treponema pallidium, Treponema pertenue, Leptospira, Rickettsia*, and *Actinomyces israelli*.

In certain embodiments, a benzo[b]azepine TLR agonist formulation of the present invention is administered in combination with an anti-bacterial agent. Non-limiting examples of anti-bacterial agents include proteins, polypeptides, peptides, fusion proteins, antibodies, nucleic acid molecules, organic molecules, inorganic molecules, and small molecules that inhibit and/or reduce a bacterial infection, inhibit and/or reduce the replication of bacteria, or inhibit and/or reduce the spread of bacteria to other cells or subjects. Specific examples of anti-bacterial agents include, but are not limited to, antibiotics such as penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketoconazole, isoniazid, metronidazole, and pentamidine.

In certain embodiments a benzo[b]azepine TLR agonist formulation of the invention is administered in combination with an anti-fungal agent. Specific examples of anti-fungal agents include, but are not limited to, azole drugs (e.g., miconazole, ketoconazole (NIZORAL®), caspofungin acetate (CANCIDAS®), imidazole, triazoles (e.g., fluconazole (DIFLUCAN®), and itraconazole (SPORANOX®)), polyene (e.g., nystatin, amphotericin B (FUNGIZONE®), amphotericin B lipid complex ("ABLC")(ABELCET®), amphotericin B colloidal dispersion ("ABCD")(AMPHOTEC®), liposomal amphotericin B (AMBISONE®)), potassium iodide (KI), pyrimidine (e.g., flucytosine (ANCOBON®)), and voriconazole (VFEND®).

5.3 Administration and Dosing

The benzo[b]azepine TLR agonists of the invention are preferably formulated for injection, most preferably subcutaneous injection. In certain embodiments, the benzo[b]azepine TLR agonists of the invention are formulated for administration by an intradermal, a transdermal, a subcutaneous, or an intramuscular route. In one embodiment, the benzo[b]azepine TLR agonists are formulated for intravenous administration. However, the benzo[b]azepine TLR agonists may be formulated for any suitable route of administration, including, by way of example, nasal (e.g., via an aerosol), buccal (e.g., sub-lingual), topical (i.e., both skin and mucosal surfaces, including airway surfaces), intrathecal, intra-articular, intraplural, intracerebral, intra-arterial, intraperitoneal, oral, intralymphatic, intranasal, rectal or vaginal administration, by perfusion through a regional catheter, or by direct intralesional injection.

The formulations of the present invention contain an amount of a benzo[b]azepine TLR agonist that is effective for the intended use. Particular dosages are also selected based on a number of other factors including the age, sex, species and condition of the patient. Effective amounts can also be extrapolated from dose-response curves derived from in vitro test systems or from animal models.

In certain embodiments, the dose of benzo[b]azepine TLR agonist is measured in units of mg/kg of body weight. In other embodiments, the dose is measured in units of mg/kg of lean body weight (i.e., body weight minus body fat content). In other embodiments, the dose is measured in units of mg/m$^2$ of body surface area. In other embodiments, the dose is measured in units of mg per dose administered to a patient. Any measurement of dose can be used in conjunction with the compositions and methods of the invention and dosage units can be converted by means standard in the art.

Examples of dosing regimens that can be used in the methods of the invention include, but are not limited to, daily, three times weekly (intermittent), weekly, or every 14 days. In certain embodiments, dosing regimens include, but are not limited to, monthly dosing or dosing every 6-8 weeks. In a preferred embodiment, a benzo[b]azepine TLR agonist formulation of the present invention is administered by subcutaneous injection weekly or biweekly in combination with a suitable treatment modality for the treatment of cancer or infectious disease in a subject, preferably a human subject. Suitable treatment modalities are described in Section 5.3 and its subsections.

Exemplary doses of a benzo[b]azepine TLR agonist include milligram amounts per kilogram of the subject. In one embodiment, the dose is from about 0.02 to 10 mg/kg of body weight or about 0.04 to 5 mg/kg of body weight. In a specific embodiment, the dosage is about 0.05 mg/kg, about 0.1 mg/kg, about 0.5 mg/kg, about 1 mg/kg, about 5 mg/kg, or about 10 mg/kg of the subject's body weight.

In certain embodiments of the methods for treating cancer or infectious disease, the benzo[b]azepine TLR agonist is administered to the subject at a dose of from about 0.02 to 10 mg/kg of body weight or about 0.04 to 5 mg/kg of body weight of the subject. In particular embodiments, the benzo[b]azepine TLR agonist is administered at a dose of about 0.05 mg/kg, about 0.1 mg/kg, about 0.5 mg/kg, about 1 mg/kg, about 5 mg/kg, or about 10 mg/kg of the subject's body weight. In certain further embodiments, the benzo[b]azepine TLR agonist formulation is administered to the subject on a weekly or biweekly basis. In specific embodiments, a daily dose is at least 0.05 mg, 0.50 mg, 1.0 mg, 5.0 mg, 10 mg, 15 mg, 20 mg, 30 mg, or at least 50 mg.

Recommended dosages for intradermal, intramuscular, intraperitoneal, subcutaneous, epidural, or intravenous administration are in the range of about 0.02 to 10 mg/kg of body weight per day. Suitable doses for topical administration are in the range of about 0.001 milligram to about 50 milligrams, depending on the area of administration. Those skilled in the art will appreciate that dosages are generally higher and/or frequency of administration greater for initial treatment as compared with maintenance regimens.

5.3.1 Exemplary Regimens for the Treatment of Cancer

In particular embodiments, the benzo[b]azepine TLR agonist formulations of the invention are used in combination with an existing treatment regimen for the treatment of cancer in a subject, preferably a human subject. In accordance with this embodiment, the benzo[b]azepine TLR agonist formulation can be administered prior to, subsequently, or concurrently with a suitable anti-cancer agent(s) for the treatment of cancer. Preferably, the administration of the benzo[b]azepine TLR agonist formulation is coordinated with the dosage and timing of the anti-cancer agent(s) depending on the type of cancer, the subject's history and condition, and the particular anti-cancer agent(s) of choice.

In one embodiment, the regimen comprises 5-fluorouracil, cisplatin, docetaxel, doxorubicin, HERCEPTIN®, gemcitabine, IL-2, paclitaxel, and/or VP-16 (etoposide) for the treatment of breast cancer. In another embodiment, the regimen comprises paclitaxel, docetaxel, mitoxantrone, and/or an androgen receptor antagonist (e.g., flutamide) for the treatment of prostate cancer. In another embodiment, the regimen comprises fludarabine, cytosine arabinoside, gemtuzumab (MYLOTARG), daunorubicin, methotrexate, vincristine, 6-mercaptopurine, idarubicin, mitoxantrone, etoposide, asparaginase, prednisone and/or cyclophosphamide for the treatment of leukemia. In one embodiment, the regimen comprises dexamethasone for the treatment of myeloma. In one embodiment, the regimen comprises dacarbazine for the treatment of melanoma. In one embodiment, the regimen comprises irinotecan for the treatment of colorectal cancer. In one embodiment, the regimen comprises paclitaxel, docetaxel, etoposide and/or cisplatin for the treatment of lung cancer. In one embodiment, the regimen comprises cyclophosphamide, CHOP, etoposide, bleomycin, mitoxantrone and/or cisplatin for the treatment of non-Hodgkin's lymphoma. In one embodiment, the regimen comprises cisplatin for the treatment of gastric cancer. In one embodiment, the regimen comprises gemcitabine for the treatment of pancreatic cancer.

The duration of treatment with the anti-cancer agent may vary according to the particular therapeutic agent used. In certain embodiments, the administration is discontinuous, i.e., daily doses are divided into several partial administrations. According to certain embodiments, the method of treatment comprises at least one cycle, preferably more than one cycle, during which a single therapeutic or sequence of therapeutics is administered. An appropriate period of time for one cycle can be determined according to routine methods by the skilled artisan, as well as the total number of cycles, and the interval between cycles.

In a specific embodiment, the regimen comprises gemcitabine at a dose ranging from 100 to 1000 mg/m²/cycle. In another embodiment, the regimen comprises dacarbazine at a dose ranging from 200 to 4000 mg/m²/cycle. In a preferred embodiment, the dose of dacarbazine ranges from 700 to 1000 mg/m²/cycle. In another embodiment, the regimen comprises fludarabine at a dose ranging from 25 to 50 mg/m²/cycle. In another embodiment, the regimen comprises cytosine arabinoside (Ara-C) at a dose ranging from 200 to 2000 mg/m²/cycle. In another embodiment, the regimen comprises docetaxel at a dose ranging from 1.5 to 7.5 mg/kg/cycle. In another embodiment, the regimen comprises paclitaxel at a dose ranging from 5 to 15 mg/kg/cycle. In another embodiment, the regimen comprises cisplatin at a dose ranging from 5 to 20 mg/kg/cycle. In another embodiment, the regimen comprises 5-fluorouracil at a dose ranging from 5 to 20 mg/kg/cycle. In another embodiment, the regimen comprises doxorubicin at a dose ranging from 2 to 8 mg/kg/cycle. In another embodiment, the regimen comprises epipodophyllotoxin at a dose ranging from 40 to 160 mg/kg/cycle. In another embodiment, the regimen comprises cyclophosphamide at a dose ranging from 50 to 200 mg/kg/cycle. In another embodiment, the regimen comprises irinotecan at a dose ranging from 50 to 75, 75 to 100, 100 to 125, or 125 to 150 mg/m²/cycle. In another embodiment, the regimen comprises vinblastine at a dose ranging from 3.7 to 5.4, 5.5 to 7.4, 7.5 to 11, or 11 to 18.5 mg/m²/cycle. In another embodiment, the regimen comprises vincristine at a dose ranging from 0.7 to 1.4, or 1.5 to 2 mg/m²/cycle. In yet another embodiment, the regimen comprises methotrexate at a dose ranging from 3.3 to 5, 5 to 10, 10 to 100, or 100 to 1000 mg/m²/cycle.

In one embodiment, the regimen encompasses the use of a low dose of a chemotherapeutic agent. In accordance with this embodiment, initial treatment of a subject with a benzo[b]azepine TLR agonist formulation of the invention increases the sensitivity of a tumor to subsequent challenge with an anti-cancer agent. Thus, the anti-cancer agent can be administered to the subject at a dose that is near or below the lower range of acceptable dosages for that agent administered alone. In one embodiment, the regimen comprises the subsequent administration of docetaxel at 6 to 60 mg/m²/day or less. In another embodiment, the regimen comprises the subsequent administration of paclitaxel at 10 to 135 mg/m²/day or less. In another embodiment, the regimen comprises the subsequent administration of fludarabine at 2.5 to 25 mg/m²/day or less. In another embodiment, the regimen comprises the subsequent administration of cytosine arabinoside (Ara-C) at 0.5 to 1.5 g/m²/day or less. In another embodiment, the regimen comprises the subsequent administration of gemcitabine at from 10 to 100 mg/m²/cycle. In another embodiment, the regimen comprises the subsequent administration of cisplatin, e.g., PLATINOL or PLATINOL-AQ (Bristol Myers), at a dose ranging from 5 to 10, 10 to 20, 20 to 40, or 40 to 75 mg/m²/cycle. In another embodiment, the regimen comprises the subsequent administration of cisplatin ranging from 7.5 to 75 mg/m²/cycle. In another embodiment, the regimen comprises the subsequent administration of carboplatin, e.g., PARAPLATIN (Bristol Myers), at a dose ranging from 2 to 4, 4 to 8, 8 to 16, 16 to 35, or 35 to 75 mg/m²/cycle. In another embodiment, the regimen comprises the subsequent administration of docetaxel, e.g., TAXOTERE (Rhone Poulenc Rorer) at a dose ranging from 6 to 10, 10 to 30, or 30 to 60 mg/m²/cycle. In another embodiment, the regimen comprises the subsequent administration of paclitaxel, e.g., TAXOL (Bristol Myers Squibb), at a dose ranging from 10 to 20, 20 to 40, 40 to 70, or 70 to 135 mg/kg/cycle. In another embodiment, the regimen comprises the subsequent administration of 5-fluorouracil at a dose ranging from 0.5 to 5 mg/kg/cycle. In another embodiment, the regimen comprises the subsequent administration of doxorubicin, e.g., ADRIAMYCIN (Pharmacia & Upjohn), DOXIL (Alza), RUBEX (Bristol Myers Squibb), at a dose ranging from 2 to 4, 4 to 8, 8 to 15, 15 to 30, or 30 to 60 mg/kg/cycle.

The above-described administration schedules are provided for illustrative purposes only and should not be considered limiting.

5.4 Kits

The present invention provides a pharmaceutical pack or kit comprising one or more containers filled with a liquid or lyophilized benzo[b]azepine TLR agonist formulation of the invention. In one embodiment, the formulation is an aqueous formulation of the benzo[b]azepine TLR agonist (1E, 4E)-2-amino-N,N-dipropyl-8-(4-(pyrrolidine-1-carbonyl)phenyl)-3H-benzo[b]azepine-4-carboxamide containing a β-cyclodextrin, preferably sulfobutylether β-cyclodextrin. In one embodiment, the formulation is lyophilized. In preferred embodiments the liquid or lyophilized formulation is sterile. In one embodiment, the kit comprises a liquid or lyophilized formulation of the invention, in one or more containers, and one or more other prophylactic or therapeutic agents useful for the treatment of cancer or an infectious disease. The one or more other prophylactic or therapeutic agents may be in the same container as the benzo[b]azepine TLR agonist or in one or more other containers. Preferably, the benzo[b]azepine TLR agonist is formulated at a concentration of from about 0.5 mg/ml to about 50 mg/ml, from about 1 mg/ml to about 40 mg/ml, or from about 2 mg/ml to about 15 mg/ml, and the formulation is suitable for injection, preferably subcutaneous injection. Preferably, the kit contains the benzo[b]azepine TLR agonist in unit dosage form. Most preferably, the unit dosage form is in a form suitable to provide a unit dose of about 0.02 to 10 mg/kg or about 0.04 to 5 mg/kg of body weight of the subject to be treated.

In certain embodiments, the kit further comprises instructions for use in the treatment of cancer or infectious disease (e.g., using the liquid formulations of the invention alone or in combination with another prophylactic or therapeutic agent), as well as side effects and dosage information for one or more routes of administration. Optionally associated with such container(s) is a notice in the form prescribed by a governmental agency regulating the manufacture, use or sale of pharmaceuticals or biological products, which notice reflects approval by the agency of manufacture, use or sale for human administration.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same.

The invention is further defined by reference to the following examples, which are not meant to limit the scope of the present invention. It will be apparent to those skilled in the art that many modifications, both to the materials and methods, may be practiced without departing from the purpose and interest of the invention.

5.5 EXAMPLES

The following are specific examples of stable aqueous and lyophilized formulations of a benzo[b]azepine TLR agonist of the present invention. The specific benzo[b]azepine TLR agonist used in these examples is (1E, 4E)-2-amino-N,N-dipropyl-8-(4-(pyrrolidine-1-carbonyl)phenyl)-3H-benzo[b]azepine-4-carboxamide. As described herein, a benzo[b]azepine TLR agonist may be formulated at concentrations of up to 40-50 mg/ml using β-cyclodextrin, preferably sulfobutylether β-cyclodextrin. Specifically, the examples describe formulations of the benzo[b]azepine TLR agonist using either 15% or 25% w/v sulfobutylether β-cyclodextrin. These formulations are stable at room temperature and at normal refrigeration temperatures. The aqueous formulation is also suitable for administration by subcutaneous injection. The aqueous formulation may also be lyophilized. An exemplary lyophilization procedure is described below. The 15% sulfobutylether β-cyclodextrin formulation is preferred for administration by subcutaneous injection following reconstitution of the lyophilized product.

5.5.1 Aqueous Formulation

A 40 mg/mL solution of a benzo[b]azepine TLR agonist is prepared as described below. Briefly, the required amount of the agonist is dissolved in 10 mM citrate, pH 2.8-3.2, containing either 25% or 15% w/v sulfobutylether β-cyclodextrin and stirred for 30 minutes. Following solubilization, the pH of the solution is adjusted to 6.5, the solution is stirred for an additional 15 minutes and filtered through a 0.2 micron polyethersulfone filter. This formulation is suitable for subcutaneous injection.

TABLE 1

Stability of aqueous formulation

| | Concentration of TLR Agonist (mg/ml) | | | |
|---|---|---|---|---|
| | Target: 40 mg/ml | | Target: 50 mg/ml | |
| Time (days) | RT | 2-8° C. | RT | 2-8° C. |
| 0 | | 38.2 | | 43.8 |
| 2 | 40.5 | 41.4 | 48.4 | 49.2 |
| 6 | 37.7 | 40.8 | 46.9 | 47.5 |
| 7 | 38.2 | 40.8 | 46.2 | 45.6 |
| 9 | 37.5 | 40.6 | 46.3 | 47.4 |

Formulations were prepared by in-process pH manipulation and filtered as described below. The filtered solutions were stored at room temperature (RT, about 23° C.) and at 2-8° C. Stored samples were removed from storage at the indicated time points and evaluated for concentration of the benzo[b]azepine TLR agonist by HPLC.

Detailed Procedure for Aqueous Formulation of benzo[b]azepine TLR Agonist

Weigh out an amount of sulfobutylether β-cyclodextrin required for a 25% w/v solution in the final volume of the formulation.

Weigh out an amount of citric acid required for a 0.19% w/v solution in the final volume of the formulation.

Weigh out an amount of VTX-378 required for a 40 mg/mL solution in the final volume of the formulation.

Transfer a volume of sterile filtered water (0.2 μm) equal to 75% of the batch volume into the container for batch manufacture. Add the citric acid and sulfobutylether β-cyclodextrin to the container for batch manufacture and stir the components at medium speed until the citric acid and sulfobutylether β-cyclodextrin dissolve completely.

Add benzo[b]azepine TLR agonist to the above solution and stir for an additional 15 min.

Adjust the pH of the formulation to 2.8-3.0 using 6N hydrochloric acid and stir at medium speed for 30 min to ensure dissolution of benzo[b]azepine TLR agonist in the medium.

Adjust the pH of the formulation to 6.3-6.7 using 6N sodium hydroxide and stir at medium speed for 15 min. Turbidity will be observed in the formulation in this pH range.

Adjust the volume of the formulation to the final volume of the batch using water and stir at medium speed for 10 min. Ensure that the pH is at 6.3-6.7.

Filter the entire batch into a container (previously rinsed with 0.1 N sodium hydroxide, 0.2 μm filtered water and filtered 70% ethanol, in that order, and dried through a sterile 0.2 μm polyethersulfone filter on a clean bench.

If desired, transfer aliquots of the filtered formulation into suitable glass containers (previously rinsed with 0.1 N sodium hydroxide, 0.2 μm filtered water and filtered 70% ethanol, in that order, and dried) using sterile disposable pipets on a clean bench.

It is recommended that the formulation be stored at 2-8° C.

5.5.2 Lyophilized Formulation

The 40 mg/mL formulation described above is lyophilized according to the following freeze-drying cycle:

Shelf Load Temperature=−50° C.

Freezing: Hold at −50° C. for 120 min; vacuum to seal chamber

Condenser and Vacuum: Condenser temperature (the temperature of the condenser at which vacuum will be enabled)=−50° C.; Heat start pressure (the pressure at which the process will continue to primary drying)=400 mTorr Primary Drying: Ramp to 0° C. in 120 min at a vacuum of 100 mTorr; Ramp to 10° C. in 80 min at a vacuum of 100 mTorr; Hold at 10° C. for 1920 min at a vacuum of 100 mTorr The lyophilized formulations prepared as described above were stable at both room temperature (about 23° C.) and at 2-8° C. for at least two months as shown in the table below. Samples were removed from storage at the indicated time point, reconstituted in 0.8 ml of water each, and evaluated for pH, osmolality, and concentration of the benzo[b]azepine TLR agonist by HPLC.

TABLE 2

Stability of lyophilized formulation

| Time (weeks) | Storage Temp (° C.) | pH | Osmolality (mOsm/kg) | Conc. of TLR agonist (mg/ml) |
|---|---|---|---|---|
| initial | NA | 6.39 | 733 | 39.9 |
| 2 | RT | 6.35 | 725 | 44.0 |
| | 2-8 | 6.37 | 736 | 39.5 |
| 4 | RT | 6.35 | 722 | 41.7 |
| | 2-8 | 6.34 | 722 | 40.1 |
| 8 | RT | 6.37 | 726 | 44.0 |
| | 2-8 | 6.37 | 730 | 44.0 |

Solutions of 40 mg/ml benzo[b]azepine TLR agonist prepared in 15% w/v sulfobutylether β-cyclodextrin (in 10 mM citrate, pH 6.5) were lyophilized as described herein. The lyophilized samples were stored at room temperature (about 23° C.) and at 2-8° C. for up to 2 months. Samples were removed from storage at the indicated time point, reconstituted in 0.8 ml of water each, and evaluated for pH, osmolality, and concentration of the benzo[b]azepine TLR agonist by HPLC.

Detailed Procedure for Lyophilized Formulation of benzo[b]azepine TLR Agonist

Weigh out the target amount of sulfobutylether β-cyclodextrin required for a 15% w/v solution in the final volume of the formulation.

Weigh out the target amount of citric acid required for a 0.19% w/v solution in the final volume of the formulation.

Weigh out the target amount of benzo[b]azepine TLR agonist required for a 40 mg/mL solution in the final volume of the formulation.

Transfer a volume of sterile filtered water (0.2 µm) equal to 75% of the batch volume into the container for batch manufacture. Add the citric acid and sulfobutylether β-cyclodextrin to the container for batch manufacture and stir the components at medium speed until the citric acid and sulfobutylether β-cyclodextrin dissolve completely.

Add benzo[b]azepine TLR agonist to the above solution and stir for an additional 30 min.

Adjust the pH of the formulation to 2.8-3.0 by adding 6N hydrochloric acid drop-wise at a rate of approximately 0.5 mL/min allowing the solution to stir for 1 min at the end of each addition of 0.5 mL. During the drop-wise addition monitor the pH continuously. Once at the desired pH, continue stirring the solution at medium speed for 30 min to ensure dissolution of benzo[b]azepine TLR agonist in the medium.

Adjust the pH of the formulation to 6.3-6.7 by adding 6N sodium hydroxide drop-wise at rate of approximately 0.5 mL/min allowing the solution to stir for 2 min at the end of each addition of 0.5 mL. During the drop-wise addition monitor the pH continuously. Ensure that the target pH is reached and do not let the solution pH to reach values greater than 6.7. Once at the desired pH, continue stirring at medium speed for 15 min. Turbidity will be observed in the formulation in this pH range.

The volume of each of 6N hydrochloric acid and 6N sodium hydroxide per incremental addition (0.5 mL) mentioned above is based on a batch size of 1 L. These volumes should be adjusted proportionally to the final batch size, e.g., for a 10 L batch the volume of each addition of acid/base will be 5 mL.

Adjust the volume of the formulation to the final volume of the batch using water and stir at medium speed for 10 min. Check that the pH is at 6.3-6.7 and adjust the pH to be within this range, if necessary, using 6N sodium hydroxide or 6N hydrochloric acid.

Filter the entire batch into a container (previously rinsed with 0.1 N sodium hydroxide, 0.2 µm filtered water and filtered 70% ethanol, in that order, and dried) through a sterile 0.2 µm polyethersulfone filter on a clean bench.

Transfer 1.2 mL aliquots of the filtered formulation into 3-mL serum vials (previously rinsed with 0.1 N sodium hydroxide, 0.2 µm filtered water and filtered 70% ethanol, in that order, and dried) using sterile disposable pipets on a clean bench.

Transfer the filled vials to the lyophilizer shelf with the grey butyl stoppers placed loosely on top of the vials to allow gas flow in and out of the vials through the spaces between the prongs of the stoppers. Use the lyophilization cycle shown in Attachment 1. Use high purity nitrogen to adjust the chamber pressure.

Upon completion of the lyophilization, release the vacuum to dry high purity nitrogen. Stopper the vials and seal the vials with aluminum crimp seals.

It is recommended that the formulation be stored at 2-8° C.

5.5.3 Stability of Inclusion Complex Formulation Versus Co-solvent Formulation benzo[b]azepine TLR agonist solutions were prepared either as an inclusion complex formulation or as a co-solvent formulation and evaluated for short-term stability as measured by concentration of benzo[b]azepine TLR agonist remaining after storage at the indicated temperature for the indicated time.

Inclusion Complex Formulation

A 5 mg/mL benzo[b]azepine TLR agonist solution was prepared in 25% w/v CAPTISOL in 10 mM citrate (pH 6.5). Briefly, the required amounts of CAPTISOL and citric acid were dissolved in a volume equivalent to ~75% of batch size. The target amount of benzo[b]azepine TLR agonist was added to this solution and stirred for 30 min. The pH of the sample was adjusted to ~3.0 using 6N HCl and stirred for 30 min. The pH was adjusted to ~6.5 using 6N NaOH and stirred for an additional 15 min. The volume of the formulation was made up to 100% of batch size using water. The formulation was then filtered through 0.2 µm polyethersulfone filter and aseptically filled into a sterile container (235 µL per container). All steps of the formulation preparation were carried out at room temperature.

Co-solvent Formulation

A 5 mg/mL benzo[b]azepine TLR agonist solution was prepared in a solvent system containing 10% propylene glycol, 10% polyethylene glycol 400 (PEG 400) and 10 mM citrate in water (pH 6.5). Briefly, the required amount of citric acid was dissolved in a volume equivalent to ~50% of batch size. The required amounts of propylene glycol and PEG 400 were added and stirred to mix. The target amount of benzo[b]azepine TLR agonist was added to this solution and stirred for 30 min. The pH of the sample was adjusted to ~3.0 using 6N HCl and stirred for 30 min. The pH was adjusted to ~6.5 using 6N NaOH and stirred for an additional 15 min. The volume of the formulation was made up to 100% of batch size using water. The formulation was then filtered through 0.2 µm polyethersulfone filter and aseptically filled into sterile containers (235 µL per container). All steps of the formulation preparation were carried out at room temperature.

Stability Evaluation

The containers filled with the inclusion complex formulation were stored either at room temperature (RT) or at 2-8° C. The containers filled with the co-solvent formulation were stored either at room temperature, at 2-8° C., or at 40° C. The samples were removed from storage at specific time-points and evaluated for benzo[b]azepine TLR agonist concentration by HPLC according to standard methods.

Results

Table 3 provides the assay concentration of the benzo[b]azepine TLR agonist in the stability samples at specific time-points and as a function of storage temperature. As shown in the table, the inclusion complex formulation did not show any significant loss of benzo[b]azepine TLR agonist up to 19 days of storage even at room temperature. In contrast, a significant loss of the benzo[b]azepine TLR agonist was observed in the co-solvent formulation after 14 days of storage at room temperature (~29% loss). The degradation of the benzo[b]azepine TLR agonist in the co-solvent formulation was more pronounced at 40° C. It should be noted that the co-solvent formulation samples stored at 40° C. and at room temperature contained insoluble material after 7 days and 14 days, respectively. Based on these stability studies, inclusion complex formulation prepared with CAPTISOL results in better stability compared to the co-solvent formulation.

TABLE 3

Stability of benzo[b]azepine TLR agonist formulations formulated either as an inclusion complex in CAPTISOL or with a co-solvent (10% propylene glycol, 10% polyethylene glycol 400)

| | | | | VTX-378 concentration (mg/mL) | | | |
|---|---|---|---|---|---|---|---|
| | Inclusion Complex Formulation | | | | Co-solvent Formulation | | |
| Time-point | 2-8° C. | RT | Time-point | 2-8° C. | RT | 40° C. |
| Initial | 5.1 | 5.1 | Initial | 4.9 | 4.9 | 4.9 |
| 7 days | 5.0 | 5.0 | 7 days | 4.9 | 4.6 | 3.2 |
| 17 days | 5.2 | 5.0 | 14 days | 4.7 | 3.5 | 2.0 |

Stability of benzo[b]azepine TLR agonist formulations. Inclusion complex and co-solvent formulations of the agonist were evaluated for stability by determining agonist concentration at specific time-points following storage at 2-8° C. and at RT (and 40° C. for co-solvent formulation).

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

We claim:

1. A stable liquid formulation comprising a Toll-like receptor (TLR) agonist and a β-cyclodextrin, wherein said agonist is (1E,4E)-2-amino-N,N-dipropyl-8-(4-(pyrrolidine-1-carbonyl)phenyl)-3H-benzo[b]azepine-4-carboxamide or a pharmaceutically acceptable salt thereof, and the formulation is an aqueous solution comprising the agonist at a concentration of from about 1 mg/ml to about 40 mg/ml and the β-cyclodextrin at a concentration of from about 1% to about 30% weight/volume, and the pH of the formulation is from about 5.0 to about 7.

2. The formulation of claim 1, wherein the β-cyclodextrin is sulfobutyl ether β-cyclodextrin.

3. The formulation of claim 1, wherein the formulation comprises from about 5%-15% weight/volume of the β-cyclodextrin.

4. The formulation of claim 1, wherein the agonist is formulated at a concentration of from about 2 mg/ml to about 15 mg/ml.

5. A method for treating cancer in a subject comprising administering to the subject a stable formulation of claim 1, and the cancer is selected from colon carcinoma, ovarian cancer, breast cancer, head and neck cancer, renal cancer, bladder cancer, hepatocellular cancer and lymphoma.

6. The method of claim 5, wherein the TLR agonist is formulated at a concentration of at least 2 mg/ml.

7. The method of claim 5, wherein the formulation is suitable for administration to the subject by injection.

8. The method of claim 5, wherein the TLR agonist is administered to the subject at weekly or biweekly intervals.

9. A method for treating an infectious disease in a subject comprising administering to the subject a stable formulation of claim 1.

10. A method for treating atopic dermatitis in a subject comprising administering to the subject a stable formulation of claim 1.

11. A pharmaceutical pack or kit comprising one or more containers filled with a stable formulation of claim 1.

12. The formulation of claim 1, wherein the formulation is stable at about 20-30° C. at concentrations up to 40 mg/ml for at least 2 weeks.

13. The formulation of claim 1, wherein the pH is about 6.5.

14. The formulation of claim 1, wherein the formulation is an aqueous solution comprising the agonist at a concentration of from about 2 mg/ml to about 15 mg/ml and the β-cyclodextrin at a concentration of from about 5% to about 15% weight/volume, and the pH of the formulation is from about 5.0 to about 7.

15. A method for treating cancer in a subject in need thereof comprising administering to the subject the formulation of claim 14, wherein the cancer is selected from colon carcinoma, ovarian cancer, breast cancer, head and neck cancer, renal cancer, bladder cancer, hepatocellular cancer and lymphoma.

* * * * *